(12) United States Patent
West

(10) Patent No.: US 6,350,367 B1
(45) Date of Patent: Feb. 26, 2002

(54) CALIBRATION METHOD USING A STABLE AND SAFE REDOX STANDARD SOLUTION

(75) Inventor: Steven J. West, Hull, MA (US)

(73) Assignee: Orion Research, Inc., Beverly, MA (US)

(*) Notice: Subject to any disclaimer, the term of this patent is extended or adjusted under 35 U.S.C. 154(b) by 0 days.

(21) Appl. No.: 09/178,011

(22) Filed: Oct. 23, 1998

Related U.S. Application Data

(63) Continuation of application No. 08/609,222, filed on Mar. 1, 1996.

(51) Int. Cl.[7] .............................................. G01N 27/26
(52) U.S. Cl. .................... 205/775; 204/400; 204/416; 436/8
(58) Field of Search ................................. 204/400, 416, 204/435; 436/8.11; 205/775, 789, 789.5

(56) References Cited

U.S. PATENT DOCUMENTS

| | | | | |
|---|---|---|---|---|
| 3,309,584 A | * | 3/1967 | Powers et al. | ............... 317/231 |
| 3,401,101 A | * | 9/1968 | Keller | |
| 3,477,958 A | * | 11/1969 | Louzos | |
| 3,911,107 A | * | 10/1975 | Krezanoski | |
| 4,001,688 A | * | 1/1977 | Marwell et al. | |
| 4,495,050 A | * | 1/1985 | Ross | |
| 4,676,931 A | * | 6/1987 | Travis | |
| 5,389,545 A | * | 2/1995 | Dahms | |
| 5,453,377 A | * | 9/1995 | Dahms | |

OTHER PUBLICATIONS

2580 Oxidation—Reduction Potential (ORP) (Proposed), Physical & Aggregate Properties (2000), pp. 2–60 to 2–63, Month Unavailable.*

* cited by examiner

Primary Examiner—T. Tung
(74) Attorney, Agent, or Firm—Ernest V. Linek; Banner & Witcoff, Ltd.

(57) ABSTRACT

The present invention is directed to a stable, non-hazardous solution for calibrating oxidation-reduction potential (ORP) measurement cells. The redox standard calibration solution of the present invention consists essentially of an aqueous solution containing the triiodide/iodide redox couple. In a preferred embodiment, the solution of the present invention consists essentially of an aqueous solution containing up to about 0.01 moles per liter of iodine ($I_2$) and at least about 1 mole per liter of potassium iodide. In a most preferred embodiment, the solution of the present invention consists of an aqueous solution of 4 molar potassium iodide (KI) and 0.0067 molar iodine ($I_2$).

10 Claims, 1 Drawing Sheet

CALIBRATION METHOD USING A STABLE AND SAFE REDOX STANDARD SOLUTION

This application is a continuation of Ser. No. 08/609,222, filed Mar. 1, 1996.

BACKGROUND OF THE INVENTION

The measurement of oxidation-reduction potential, also called ORP or redox potential, is useful for characterizing the chemical properties of substances, usually aqueous solutions. The value of the redox potential is indicative of the presence and relative concentrations of oxidizing or reducing substances in a solution. For example when applied to the characterization of natural waters, the redox potential may indicate whether the normal level of dissolved oxygen has been depleted by chemical pollutants or biological activity. The measurement is made using a potentiometric cell consisting of an inert metal electrode, usually platinum, and a standard reference electrode. The standard reference electrode may be the normal hydrogen electrode (NHE), the saturated calomel electrode (SCE), or various other reference electrodes, for example, those based on silver in combination with silver chloride.

Since meaningful comparison of redox potentials can only be made when the type of cell used to make the measurement is specified, and since a user may not know the exact nature of the reference electrode when comparing cells from different manufacturers, calibration solutions are used to null out cell differences. These solutions contain "reversible redox couples" in the parlance of electrochemistry. A redox couple is a pair of species composed of the same element, but in different states of oxidation. These species are interconvertible by means of a redox reaction, that is, a chemical reaction which involves gain or loss of an electron or electrons. Redox couples which are readily interconvertible, that is, which show no resistance to undergoing interconversation when the redox potential of a solution changes due to addition of oxidizing or reducing substances, are referred to as reversible redox couples. It is these reversible redox couples which are useful in formulating redox standard solutions. Unfortunately, most redox couples are not stable in the presence of air and water; they usually revert entirely to one or the other of the two oxidation states. Thus the choice of redox couples suitable for formulating redox standard solutions is limited.

INFORMATION DISCLOSURE

Two redox standard solutions are described in *Standard Methods for the Examination of Water and Wastewater*, 18th Ed., 1992. The first, called Zobell's Solution, contains the redox couple iron(III)hexcyanoferrate and iron(II) hexacyanoferrate, also known as ferricyanide/ferrocyanide. The second standard solution, called Light's Solution, contains the redox couple iron(III) and iron(II), also know as ferric/ferrous. Each of these redox standard solutions has its disadvantages, as discussed below.

Zobell's Solution is known to be unstable when exposed to ordinary indoor lighting. In addition, this solution carries the stigma of containing cyanide groups. Light's Solution is not light-sensitive and is generally more stable than Zobell's Solution, but Light's Solution is so strongly acidic (pH about 0.3) that it can easily burn the skin of the user and it readily destroys fabrics such as cotton.

In view of the disadvantages of these two commonly employed redox standard solutions, there is a clear need for a safe and reliable redox standard solution. The present invention fills this need.

As discussed in greater detail below, the present invention is based upon the use of a known redox couple, the triiodide/iodide redox couple. One previous use of an triiodide/iodide redox couple in a mixture with other ingredients is taught in U.S. Pat. No. 4,495,050. This patent, the disclosure of which is hereby incorporated herein by reference, describes and claims a potentiometric electrode which includes an internal, ionically-conductive filling or electrolyte which is electrically coupled to an external lead. As taught therein, the electrode includes a body of electrolytic material within a container, in which the electrolyte consists of a phosphate buffer, (0.05 M $NaH_2$-$H$-$PO_4$) to fix the activity of hydrogen ions, and a redox couple consisting of 4 molar potassium iodide (KI) and 0.0067 molar iodine ($I_2$) in water ($H_2O$), buffered with 0.02 molar boric acid ($H_3BO_3$), adjusted to a pH of 7.15 with potassium hydroxide (KOH). The reference half cell has the same lead and electrolyte, although the buffer may be omitted. Nothing in this patent either teaches or suggests the independent use of an aqueous solution consisting essentially of the triiodide/iodide redox couple for the formation of a redox standard calibration solution as taught and claimed herein.

SUMMARY OF THE INVENTION

One embodiment of the present invention is directed to a redox standard solution which is both safe (e.g., to skin and fabrics) and more stable (e.g., to heat and light) than either Zobell's Solution or Light's Solution. The redox standard solution of the present invention consists essentially of an aqueous solution containing the redox couple triiodide/iodide. Advantageously, the present invention consists essentially of an aqueous solution containing a maximum of about 0.01 moles per liter of iodine and a minimum of at least about 1 mole per liter of potassium iodide. As discussed in detail below, such a redox standard solution overcomes the disadvantages of the two prior art standard solutions, providing the user with a safe, stable and reliable standard solution for ORP measurement calibrations.

Another embodiment of the present invention is directed to a method of calibrating a potentiometric cell comprising an inert metal electrode and a standard reference electrode;

said calibration method comprising measuring the oxidation-reduction potential of a redox standard calibration solution which standard solution consists essentially of an aqueous solution containing the triiodide/iodide redox couple. Preferably, the calibration measurement is made using a standard solution which consists essentially of an aqueous solution containing up to about 0.01 moles per liter of iodine ($I_2$) and at least about 1 mole per liter of potassium iodide. Most preferably, the calibration measurement is made using a standard solution which consists of an aqueous solution of 4 molar potassium iodide (KI) and 0.0067 molar iodine ($I_2$).

DETAILED DESCRIPTION OF THE PREFERRED EMBODIMENTS

The redox standard solution of the present invention is based upon the redox couple triiodide/iodide. The triiodide/iodide redox couple has been found to be a stable, non-hazardous, alternative ORP standard calibration solution. A solution made from iodine (about 0.01 moles/L) and a much larger amount of potassium iodide (from about 1, up to about 4 moles/L) endures prolonged exposure to air at 80° C. with no loss of iodine vapor; it is not light-sensitive or subject to air oxidation, and can be stored in glass or polyethylene.

Referring in detail to the Figures accompanying this specification, the stability of a redox standard solution prepared according to the preferred formulation of this invention verses Zobell's Solution and/or Light's Solution is very clear.

Figure 1:
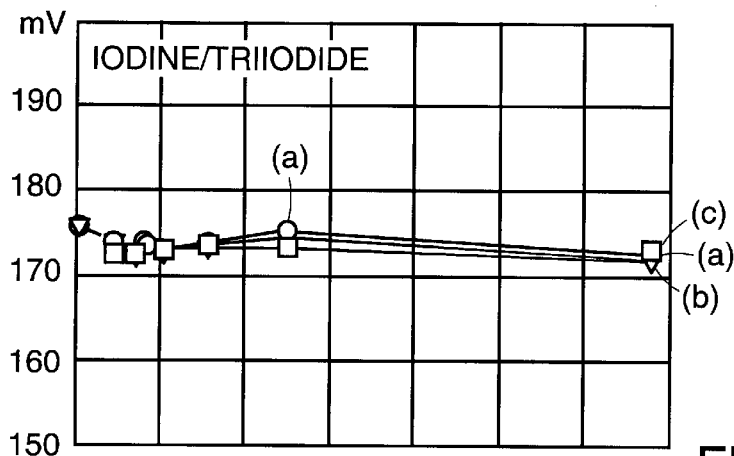
FIG. 1 is a graphical representation illustrating the stability over time of the preferred standard solution of the present invention (measured in mV) under three different storage conditions; Condition (a), storage in a glass container, at room temperature, in the dark; Condition (b), storage in a translucent plastic container, at room temperature, exposed to laboratory (indoor) light; and Condition, (c) storage in a translucent plastic container, at a constant temperature of 40° C., in the dark; each over a period of 0 to over 300 days.
Figure 2:
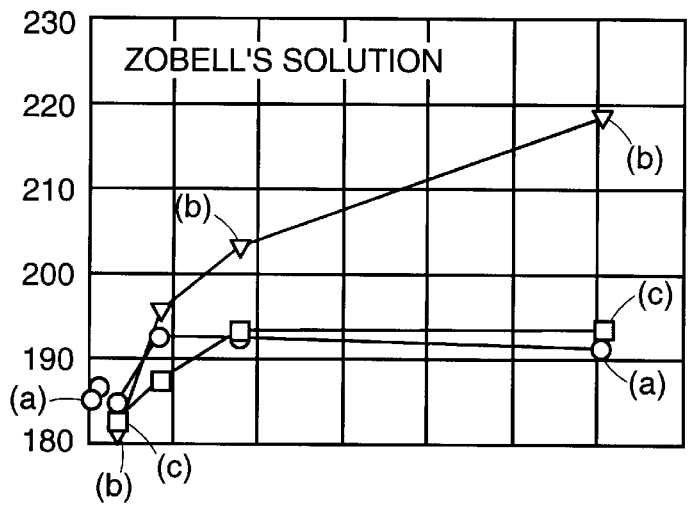
FIG. 2 is a graphical representation illustrating the instability over time of Zobell's Solution (measured in mV) when exposed to Conditions (a), (b) and (c) as identified above for FIG. 1, over a period of 0 to 300 days.
Figure 3:
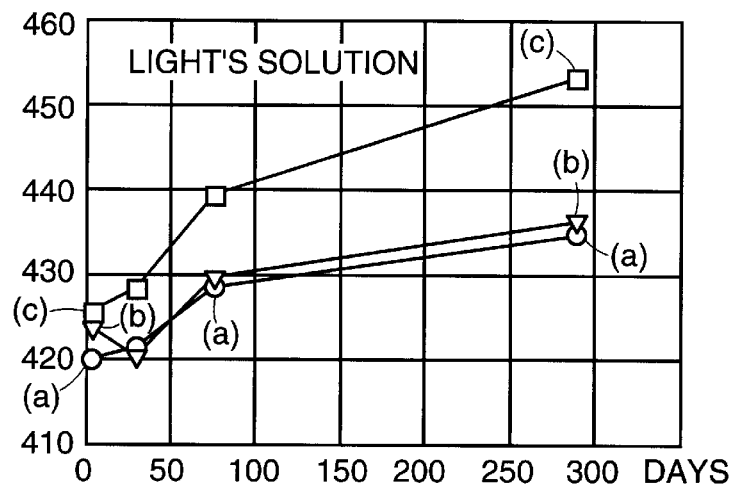
FIG. 3 is a graphical representation illustrating the instability over time of Light's Solution (measured in mV) when exposed to conditions (a), (b) and (c) as identified above for FIG. 1, over a period of 0 to just under 300 days.

The FIGS. (1, 2, and 3) illustrate the superior performance of the preferred redox standard solution of this invention over the performance of the two best known prior art standard solutions, Zobell's Solution and/or Light's Solution. The potential of a platinum electrode in the preferred redox standard solution of this invention was found to be +173 mV verses SCE and did not vary by more than 2 mV over a period of one year at 40° C. or with exposure to laboratory light. In marked contrast thereto, both Zobell's Solution and Light's Solution showed considerable changes under identical test conditions (see FIGS. 1, 2 and 3).

As illustrated, the preferred standard solution of the present invention clearly out-performs both Zobell's and Light's Solutions, by enduring prolonged exposure to heat (40° C.) with no significant loss stability over time; by not being light-sensitive; and by not being subject to air oxidation. The preferred redox standard solution of the present invention needs no special storage conditions; it can be stored in clear glass or polyethylene, without loss of stability.

Finally, the half-cell potential verses a constant temperature reference of the standard solution of this invention does not vary by more than 2 mV in the range of 5 to 60° C., indicating that the preferred redox standard solution of this invention provides fast equilibration under changing temperature conditions.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of calibrating a potentiometric cell, said cell comprising an inert metal electrode and a standard reference electrode;

said calibration method comprising measuring the oxidation-reduction potential of a redox standard calibration solution by contacting both the inert metal electrode and the reference electrode with said solution;

wherein said redox standard calibration solution consists of a reversible redox couple;

and wherein said redox standard calibration solution is stable at 40° C. up to a period of one year.

2. The calibration method of claim 1, wherein the redox standard calibration solution consists of an aqueous solution of 4 molar potassium iodide (KI) and 0.0067 molar iodine ($I_2$).

3. The method of claim 1, wherein the redox standard calibration solution consists of an aqueous solution containing a triiodide/iodide redox couple.

4. The method of claim 1, wherein the redox standard calibration solution is stable upon exposure to light.

5. The method of claim 1, wherein the redox standard calibration solution is not subject to air oxidation upon exposure to air.

6. A method of calibrating a potentiometric cell, said cell comprising an inert metal electrode and a standard reference electrode;

said calibration method comprising measuring the oxidation-reduction potential of a redox standard calibration solution by contacting both the inert metal electrode and the reference electrode with said solution;

wherein the calibration measurement is made using a redox standard calibration solution which consists of an aqueous solution containing up to about 0.01 moles per liter of iodine ($I_2$) and at least about 1 mole per liter of potassium iodide; and wherein said redox standard calibration solution is stable at 40° C. up to a period of one year.

7. A method of calibrating a potentiometric cell, said cell comprising an inert metal electrode and a standard reference electrode;

said calibration method comprising measuring the oxidation-reduction potential of a redox standard calibration solution by contacting both the inert metal electrode and the reference electrode with said solution;

wherein said redox standard calibration solution consists of a reversible redox couple; and wherein said redox standard calibration solution is stable over a temperature range of from about 5° C. to 60° C. up to a period of one year.

8. The method of claim 7, wherein the redox standard calibration solution consists of an aqueous solution containing a the triiodide/iodide redox couple.

9. The method of claim 7, wherein the redox standard calibration solution consists of an aqueous solution containing up to about 0.01 moles per liter of iodine ($I_2$) and at least about 1 mole per liter of potassium iodide.

10. The method of claim 7, wherein the redox standard calibration consists of an aqueous solution of 4 molar potassium iodide (KI) and 0.0067 molar iodine ($I_2$).

* * * * *